United States Patent [19]

Akers et al.

[11] Patent Number: 4,534,758
[45] Date of Patent: Aug. 13, 1985

[54] CONTROLLED RELEASE INFUSION SYSTEM

[75] Inventors: Michael J. Akers, Greenwood; William W. Hargrove, Indianapolis; Dale C. Harris, Fairland, all of Ind.; Charles R. Sperry, Westport, Conn.

[73] Assignee: Eli Lilly & Company, Indianapolis, Ind.

[21] Appl. No.: 514,268

[22] Filed: Jul. 15, 1983

[51] Int. Cl.³ ............................................. A61M 5/14
[52] U.S. Cl. ....................................... 604/85; 604/84; 604/86; 604/247; 604/248; 604/249; 604/411
[58] Field of Search ..................... 604/30–33, 604/56, 80–85, 122, 245–249, 405, 411, 414; 137/38, 512, 588; 141/21, 302, 306, 319, 320

[56] References Cited

U.S. PATENT DOCUMENTS

| 2,573,576 | 10/1951 | Klumb . | |
|---|---|---|---|
| 2,848,996 | 8/1958 | Kowal | 604/85 |
| 3,128,917 | 4/1964 | Krause . | |
| 3,678,959 | 7/1972 | Liposky | 604/33 |
| 3,857,392 | 12/1974 | Ogle . | |
| 3,889,687 | 6/1975 | Harris et al. | 604/10 |
| 3,931,818 | 1/1976 | Goldowsky . | |
| 4,047,527 | 9/1977 | Kelsen | 604/83 |
| 4,068,681 | 1/1978 | McNair et al. | 137/588 |
| 4,141,379 | 2/1979 | Manske . | |
| 4,237,880 | 12/1980 | Genese . | |
| 4,252,116 | 2/1981 | Genese et al. . | |
| 4,258,712 | 3/1981 | Harms et al. . | |
| 4,269,213 | 5/1981 | Sasaki | 137/38 |
| 4,332,247 | 6/1982 | Mittleman et al. | 604/82 |
| 4,392,850 | 7/1983 | Elias et al. . | |
| 4,392,851 | 7/1983 | Elias . | |
| 4,397,335 | 8/1983 | Doblar et al. | 604/32 |
| 4,424,056 | 1/1984 | Urquhart et al. | 604/56 |
| 4,465,471 | 8/1984 | Harris et al. | 604/85 |

FOREIGN PATENT DOCUMENTS

| 1122616 | 11/1956 | France . | |
|---|---|---|---|
| WO81/01241 | 5/1981 | PCT Int'l Appl. . | |
| 0275821 | 8/1927 | United Kingdom | 604/84 |
| 1461161 | 1/1977 | United Kingdom . | |
| 2083141 | 3/1982 | United Kingdom | 604/30 |

Primary Examiner—John D. Yasko
Assistant Examiner—Michelle Lester
Attorney, Agent, or Firm—Barnes & Thornburg

[57] ABSTRACT

Valved adaptors are disclosed permitting the introduction of a drug-containing vial in the delivery tube of an I.V. administration set. The adaptors have a three position operation characterized by a bypass mode, a dilution mode, and a delivery mode, the adaptors being manually changed from mode to mode. The disclosed adaptors include gravity operated valves, reciprocating spool valves, and rotating spool valves, each including a spike to penetrate the stopper of a vial and a vent to permit air to escape the vial as liquid is introduced to dilute the vial contents.

11 Claims, 16 Drawing Figures

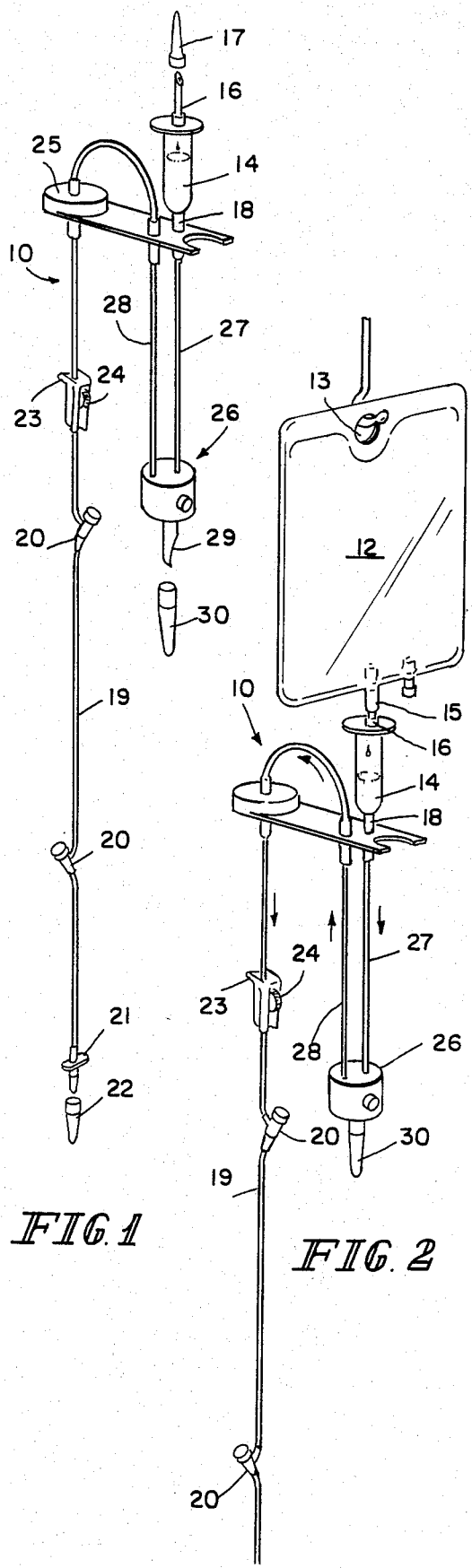
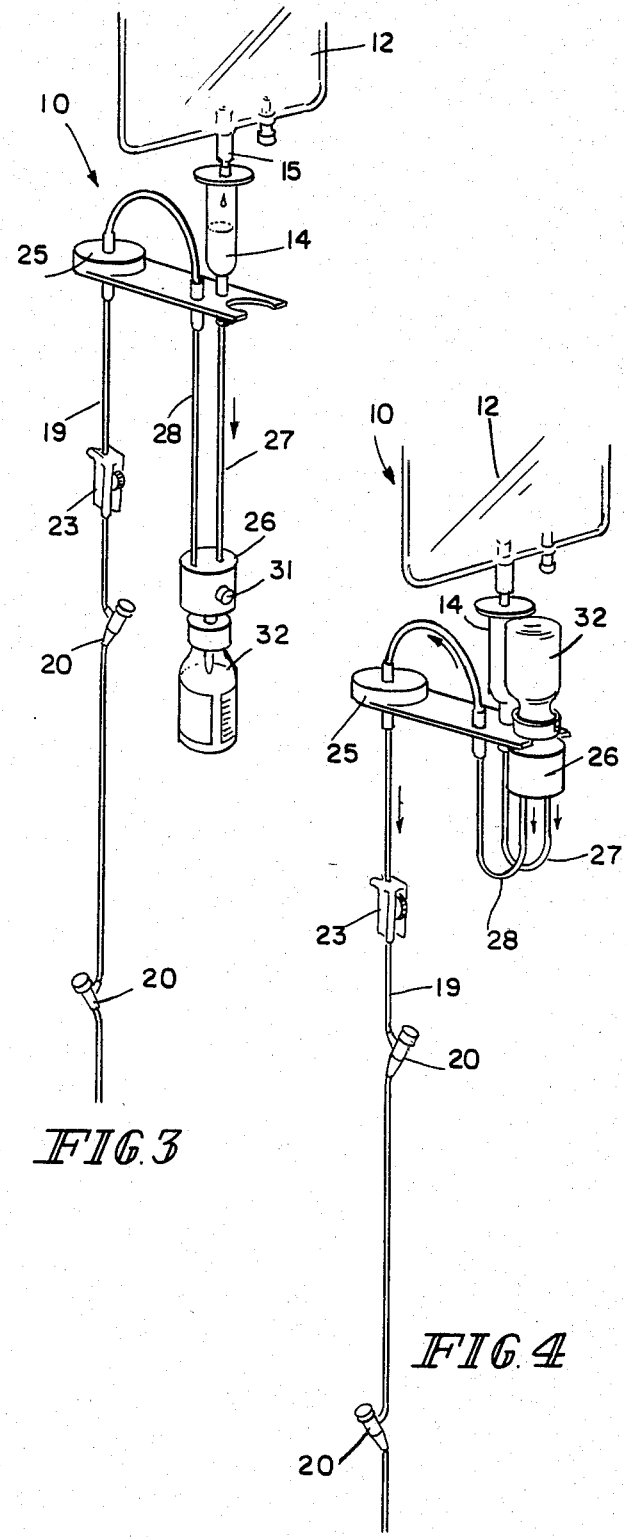
FIG. 1  FIG. 2  FIG. 3  FIG. 4

CONTROLLED RELEASE INFUSION SYSTEM

This invention relates generally to systems for intravenously administering medicine to a patient and more particularly to a system for reconstituting a drug from a dried state to a liquid state while the drug is still within the conventional drug-containing vial and thereafter administering the reconstituted drug by means of a primary intravenous administration set into which the drug vial is serially connected by means of a valve adaptor.

Conventional medical treatment frequently requires the intravenous administration of fluids and medicated solutions. Such fluids can include saline and dextrose solutions as well as other solutions to correct imbalances in body chemistry and medication solutions to treat disease. Many such solutions are frequently available in commercial antiseptic solution containers that are adapted to be punctured at one end and to be hung by the other end so that their liquid contents may be removed and infused in a vein of a patient by means of primary intravenous administration set, commonly referred to as an I.V. set.

In effecting such treatment, the closure of the solution container is punctured by a spike on the upper end of the delivery tube or conduit of the I.V. set so as to conduct the liquid material from the solution to a hypodermic needle or butterfly situated for injection into a vein of the patient.

Such I.V. sets generally also include a transparent drip chamber which includes the conduit-forming spike at the upper end which is intended to perforate and enter the solution container. The transparent drip chamber is generally employed as a means to measure the administration rate of the fluid to the patient, the rate typically being measured in drips per minute. A transparent flexible plastic tube is generally attached to the lower end of the drip chamber and a regulating clamp is provided as means to control the flow of liquid through the passageway of the plastic tube. One or more Y injection sights can be provided to attach other medicament dispensers. The I.V. set may also include a peristaltic pump to control the rate of delivery of fluid to the patient as well as a particle filter and air eliminator to insure that no air or small particles of medicine or foreign matter enter into the vein of the patient. Generally the use of conventional I.V. sets requires aseptic techniques and the I.V. set is protected against contamination during handling at the point of attachments by appropriate protective end caps and the like.

Certain of the medicines which are desirably administered to a patient by an intravenous administration set are manufactured and packaged in dry form due principally to their instability in liquid solution. The drug in dry form is typically commercially delivered in a standard glass vial containing one or two grams of the medication. The glass vial is closed with a rubber stopper and crimped aluminum seal, the aluminum seal usually having a flip off plastic cover intended to keep the top of the rubber stopper clean and to provide a means of tamper evidence. The glass vial itself is generally sized to accommodate about 10 to 15 cubic centimeters.

To reconstitute the dried drug compound, the general practice in the prior art was to remove the plastic seal exposing the rubber stopper and, after wiping the stopper with an aseptic wipe, adding five to ten cc's of sterile water diluent by inserting the needle of a syringe through the rubber stopper and depositing the contents of the syringe into the vial. One would then shake the vial to make sure the drug compound within the vial was fully dissolved or suspended in the diluent to form a reconstituted drug solution. This reconstituted solution was then withdrawn from the vial by means of a syringe, the needle of which was again inserted through the rubber stopper. The reconstituted solution was then typically injected into a plastic or glass container which had been previously filled with 50 or 100 cc's of a compatible I.V. diluent such as sterile water with a small percentage of dextrose of sodium chloride added. This container containing the fully diluted drug was then attached to the I.V. administration set with a separate drip chamber usually at a Y site and hung slightly above the primary I.V. source container.

If the reconstituted drug was not intended for immediate use, it was generally stored under a refrigerated condition until such time as the patient was ready for its administration. Once a drug compound has been reconstituted, however, a degradation of the compound begins. Refrigeration will slow this process but it is generally accepted practice to administer the reconstituted drug within a few hours, or at most one or two days so as to prevent any substantial degradation of the drug compound. Due to many influences such as patient reactions to the drug, patient recoveries, and the like, substantial percentages of the reconstitued drugs are not used within the acceptable time limits and must be discarded. Some of the drug compound itself is lost during the reconstitution steps as it is difficult to remove all of the reconstituted solution from the original drug containing vial by means of the syringe and needle. For this reason, the general commercial practice is to over fill the vials by approximately 7%. Other losses of the drug occur as the fully reconstituted container empties into the Y site through a drip chamber, some of the drug remains undelivered in the drip chamber. All of these losses tend to increase the cost of drugs to the ultimate purchaser, whether that be the patient or an insurance company.

The present invention provides a system for the administration of medicines which are typically packaged in standard small glass vials by providing a valve adaptor to a primary intravenous administration set which adaptor serially connects the drug containing vial directly to the primary delivery tube of the I.V. set in such a fashion as to permit administration of the contents of the vial to the patient. The valve adaptor includes means operable to a first and a second position providing for the dilution of the contents of the vial in the first position with liquid from the primary I.V. solution container, and after the drug is resuspended within the vial, the valve means permits delivery of the diluted contents of the vial in the second position directly to the primary I.V. passageway.

The invention has the advantage of permitting the use of the conventional glass vial as the mixing and dispensing chamber for the drug thereby reducing the chance of contamination of the drug and minimizing exposure of hospital personnel to the compound. This use of the conventional small drug containing vial as the mixing and delivery chamber after connection with the primary I.V. set eliminates any separate reconstitution in a hospital pharmacy, and the consequent need for refrigeration, and reduces storage space requirements. The invention also has been found to deliver an increased quantity of the drug in question, thereby substantially eliminating the need for the 7% over fill typically practiced in the industry. This system is intended to permit the administration of different medicines at scheduled intervals and can be used with most standard I.V. system components.

Additional features and advantages of the invention will become apparent to those skilled in the art upon consideration of the following detailed description of prefered embodiments exemplifying the best mode of carrying out the invention as presently preceived. The detailed description particularly refers to the accompanying figures in which:

FIG. 1 is a schematic illustration of a primary I.V. administration set including a valved adaptor of the present invention.

FIG. 2 is a view similar to that of FIG. 1 including a primary liquid container.

FIG. 3 is a view similar to FIG. 2 showing the addition of a conventional drug containing vial to the valved adaptor.

FIG. 4 is a view similar to FIG. 3 showing the valved adaptor and drug containing vial in the dispensing position.

Figure 5:
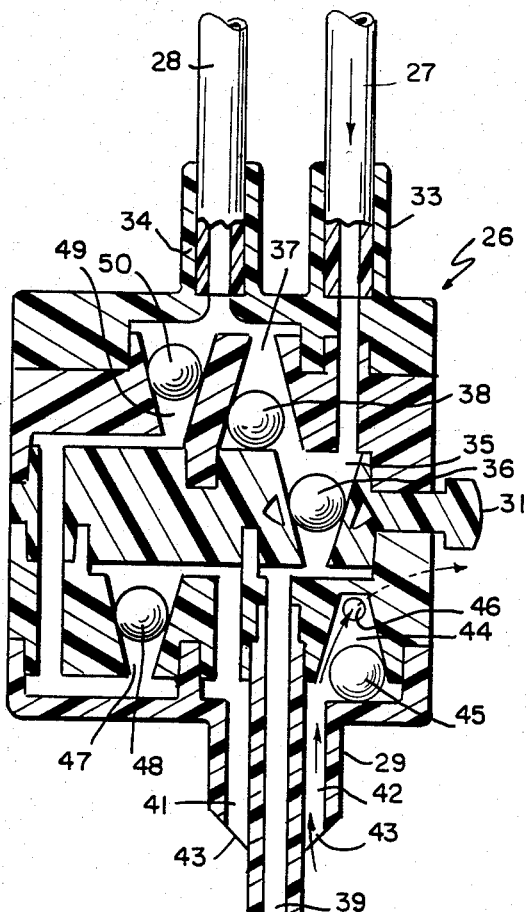
FIG. 5 is a sectional view of one embodiment of the valved adaptor shown in the upright position.

The system 10 of this invention is shown schematically in FIGS. 1 through 4 to include a container 12 containing a source of liquid for delivery to a patient, not illustrated. The source of liquid 12 can be any conventionally employed source such as the type manufactured by Travenol Laboratories, Inc., of Deerfield, Ill., 60015, and sold under the registered trademark VIAFLEX as a single dose container. Generally such containers are clear and include means 13 for suspending the container above the patient. A drip chamber 14 generally included with a conventional I.V. set includes a spike 16 adapted to perforate and enter closure 15 on the lower end of container 12. Prior to its insertion into the closure 15, the spike 16 is protected by cover 17 so as to prevent contamination of the spike and conduit within the spike. The drip chamber 14 is formed from transparent material, typically plastic to permit visual monitoring of the rate at which liquid is being administered to the patient. The lower end 18 of the drip chamber is connected to a conduit 19 typically formed of a transparent flexible plastic tube intended to carry the liquid from the drip chamber 14 to the patient. One or more Y injection sites 20 can be provided for the connection of additional sources of fluids and medicines to the system. The Y injection sites provide a sterile access to the passageway within the tubing 19. Each Y injection site 20 is closed by a standard rubber stopper adapted to receive a hypodermic needle or the like in a sterile fashion. A luer needle adaptor 21 is provided at the lower end of the I.V. system. The adaptor permits the connection of the lower end of the I.V. tubing to a hypodermic needle inserted in a vein of the patient. The lower end of the needle adaptor 21 is typically protected by a cover 22 until the system is ready for use. A clamp 23 is provided at some point along the tubing 19 for regulating the flow through the tubing. The clamp 23 includes a serrated roller 24 which engages the outer surface of the flexible plastic tube 19 to pinch the tube to a desired degree thereby imposing a restriction upon the size of the passageway within the tubing and hence controlling the rate at which liquid from the container 12 passes through the tubing 19. A conventional particle/air filter 25 such as a Model 2C0251 available from Travenol Laboratories can also be included for preventing air or particles of medicine or foreign matter from entering the lower portion of the I.V. system. All of the components previously mentioned are conventionally available and except the particle/air filter 25 are distributed by Ivac Corporation of San Diego, Calif. 92121.

In accordance with the present invention, a valved adaptor 26 is connected to the previously described portions of the primary I.V. administration set by two short lengths of tubing 27 and 28. The lower end of the valved adaptor includes a spike 29 protected until use with a cover 30. The valved adaptor 26 is designed such that when not in use as shown in FIG. 2, liquid from the container 12 passes through drip chamber 14 down short tubing segment 27 through the valved adaptor 26 and back up short tubing section 28 to the remaining portion of the I.V. administration set. The rate of delivery of liquid from the container 12 to the patient can be adjusted by clamp 23 while visually inspecting the drip rate in drip chamber 14 in the conventional fashion.

At such time as one desires to administer a drug by way of the primary I.V. administration set shown, the cover 30 is removed exposing spike 29. The spike 29 is then forced through the rubber stopper of a conventional drug containing glass vial to the position shown in FIG. 3. The valved adaptor is then manually actuated by means of a valve push button 31 which causes liquid from container 12 to enter the drug containing vial 32. As the fluid from container 12 enters vial 32, the valve 26 also permits air to escape from the vial 32. The amount of liquid delivered to the vial 32 can be controlled by the length of time the manual valve actuator button 31 is depressed. Typically, it is expected that 5 or 10 cc's of the liquid from container 12 will be delivered to vial 32 whereupon the drug containing vial 32 with the 10 cc's of liquid will be agitated for a time sufficient to suspend the previously dry medicine. It will be appreciated, that certain medicines already come in a liquid form in similar vials. In such a case, the liquid medicine may be administered to the patient without performing this initial dilution and agitation step.

Once the medicine in the vial 32 is in a liquid form, the vial 32 and valved adaptor 26 are inverted to the position shown in FIG. 4. The valved adaptor 26 of the present invention is so constructed such that when moved to a position such that the drug vial 32 is inverted, liquid from the container 12 passing through drip chamber 14 enters the vial through short tubing segment 27 and exits from the vial through short tubing segment 28, the rate of delivery of the liquid being maintained by clamp 23 in the usual fashion. In this way, the contents of the primary I.V. administration container 12 washes through vial 32 to effect delivery of the totallity of the drug contained within the vial to the patient.

Figure 6:
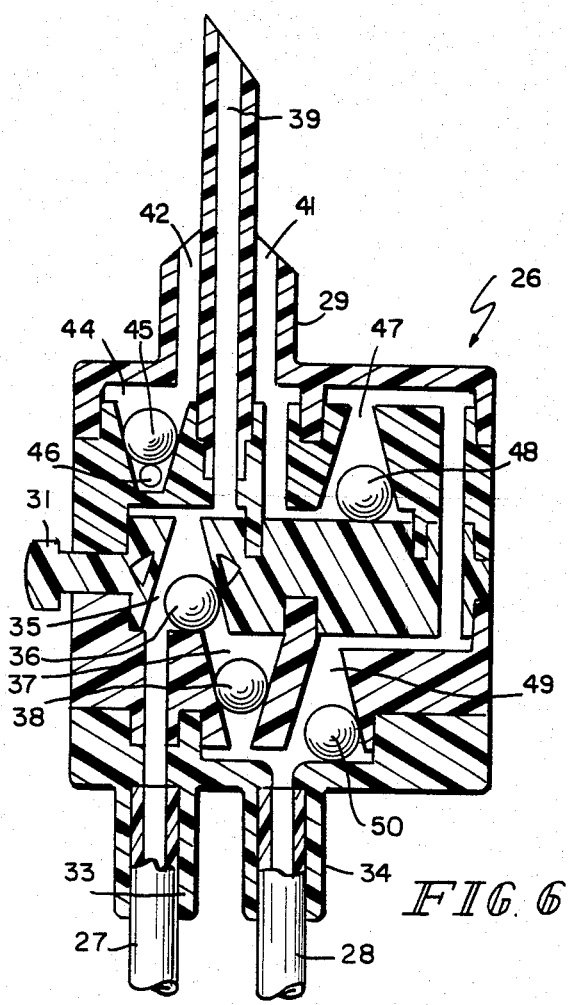
FIG. 6 is a view of the valved adaptor shown in FIG. 5 in its inverted drug delivery position.

The valved adaptor 26 can be formed in any of several configurations. A first configuration for such an adaptor is shown in section in FIGS. 5 and 6. FIG. 5 illustrates the adaptor 26 in the upright position as illustrated in FIGS. 1–3, while FIG. 6 shows the adaptor 26 in the inverted drug delivery position as illustrated in FIG. 4. The adaptor 26 includes an entry port 33 to which the short tubing segment 27 is attached and an exit port 34 to which short tubing segment 28 is attached. In the position shown in FIG. 5, fluid entering valve 26 through entry port 33 passes into a first conical valve chamber 35 which is closed by ball 36 which prevents the fluid from passing downward any further and instead causes the fluid to pass upward into conical valve chamber 37 which contains ball 38 shown in an open position. The fluid passes through valve chamber 37 upwardly out exit port 34. The valve 26 thus acts to direct fluid from the short tubing segment 27 to the short tubing segment 28 and bypass the rest of the valve structure.

The spike 29 of valve 26 shown in FIG. 5 is seen to include a central inlet port 39 including a sharpened lower edge 40 to permit easy insertion of the spike through the rubber stopper of vial 32. Two additional ports 41 and 42 are provided on opposite sides of the central port and have a tapered lower edge 43 which permits the spike to be inserted in the rubber stopper to a point where all three ports 39, 41 and 42 communicate with the interior of the vial 32 when the vial is situated as shown in FIG. 3. To dilute the contents of the drug containing vial 32, one manually actuates push button 31 causing the walls of conical valve chamber 35 to deform from their circular cross section to an oval cross section whereby fluid entering entry port 33 may pass by ball 36 down into the vial 32 through the central opening 39 in spike 29. As the fluid enters the vial through central opening 39, air is permitted to exit from the vial 32 through valve chamber 44, past ball 45 which is gravitationally situated in an open position, and out an air pervious liquid barrier situated in aperture 46. Material for forming such an air pervious liquid barrier is conventionally available and comprises a fluro plastic material sold by the Fluro Techniques Corporation under their designation M8A2000. The ball valves 47 and 49 act to prevent air from entering the primary I.V. system when the valve is in its upright position as shown in FIG. 5. When the push button 31 is released, the walls of the valve chamber 35 resume their circular cross section and are sealed by ball 36 to prevent any further entry of fluid into vial 32. The drug containing vial 32 having the desired amount of liquid therein can then be agitated to suspend or dissolve the medication in the liquid.

The valve 26 and vial 32 are then inverted from the position shown in FIGS. 3 and 5 to the drug delivery position shown in FIGS. 4 and 6. In this position, fluid from container 12 enters entry port 33 through the short segment of tubing 27 to valve chamber 35 which is now open by virtue of ball 36 being gravitationally disengaged from the conical surface of chamber 35. Additionally, ball 38 is now seated in conical valve chamber 37 so as to prevent any bypass of fluid to the outlet port 34. Instead, the fluid entering inlet port 33 is directed upward through central opening 39 in spike 29 and into the drug containing vial 32. The ball 45 is seated in chamber 44 so as to prevent the exit of any material through opening 42 to port 46. Rather, the fluid contents of vial 32 flows into exit port 41 and passes through open valves 47 and 49 containing balls 48 and 50 respectively to exit port 34 where the drug containing fluid now enters tubular member 28. When the valved adaptor 26 is in the inverted position shown in FIG. 6, fluid from the container 12 is directed continuously in inlet port 33 through valve 35 and central port 39 of spike 29 to the drug containing vial 32 whereupon the contents of the vial are emptied out through exit port 41 through valves 47 and 49 and finally out exit port 34. The contents of the drug vial 32 is thus continuously washed by the contents of the primary I.V. container 12 until all remaining traces of the drug within the vial 32 are removed and delivered to the patient.

Figure 7:
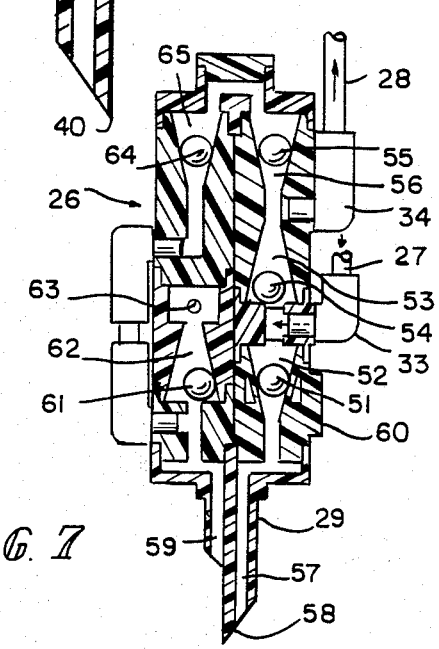
FIG. 7 is a sectional view of another embodiment of the valved adaptor shown in the upright position.
Figure 8:
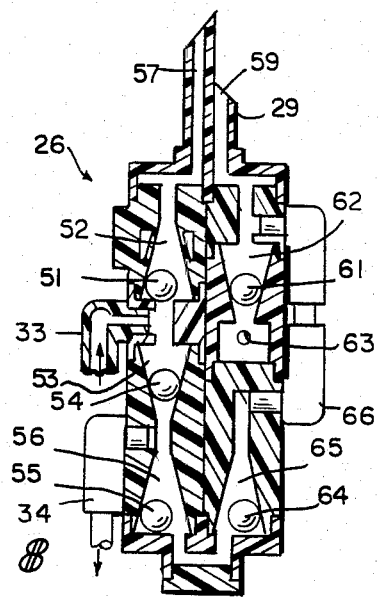
FIG. 8 is a sectional view of the valved adaptor shown in FIG. 7 in the inverted drug delivery position.

Another gravitationally operated valved adaptor 26 in accordance with the present invention is shown in FIGS. 7 and 8 having entry port 33 and exit port 34 connected to the short lengths of tubing 27 and 28 respectively. Liquid from the container 12 entering the entry port 33 of valve 26 in its upright position as shown in FIG. 7 is prevented from descending to the drug vial by means of ball 51 sealing conical valve chamber 52. The liquid is thus directed upwardly into valve chamber 53 past ball 54. The liquid is prevented from travelling further due to ball 64 sealing valve chamber 65 and hence the liquid exits through exit conduit 34. In this position, the fluid bypasses any contact with the remaining portion of the valved adaptor 26.

The valved adaptor 26 shown in FIG. 7 includes a spike 29 having an entry passageway 57 which descends to the lower end 58 of spike 29 and a shorter exit passageway 59 which terminates at a point sufficiently near the upper end of spike 29 as to permit the minimum penetration through a rubber stopper of a conventional drug containing vial. To dilute the contents of the drug containing vial, button 60 is manually actuated which deforms the wall of valve chamber 52 from its circular cross section to a more oval cross section thereby admitting fluid from entry port 32 past ball 51 down entry port 57 into the drug containing vial 32. Simultaneous with the entry of the fluid past ball 51, air is permitted to exit from the vial through exit port 59 past ball 61 in valve chamber 62 and out aperture 63 which is again sealed by an air pervious liquid barrier as previously described in connection with FIGS. 5 and 6. While the air can exit through opening 63, it is unable to pass through to exit port 34 due to the presence of ball 55 sealing valve chamber 56.

When the desired amount of fluid enters the drug containing vial 32 and the vial is sufficiently agitated to dissolve and resuspend the drug within the vial, the vial 32 and valved adaptor 26 are again inverted as shown in FIGS. 4 and 8 which causes the balls 51, 54, 55, 61, and 64 to move within their respective chambers from the position shown in FIG. 7 to that shown in FIG. 8. Thus, ball 54 closes valve chamber 53 thereby preventing the fluid entering entry port 33 from bypassing the remaining portion of the valved adaptor 26. Instead, the fluid enters the now open valve chamber 52 by-passing ball 51 and proceeds upwardly through the elongated entry port 57 of spike 29 into the drug containing vial 32. The fluidized contents of the drug containing vial 32 enters the exit port 59 and proceeds downwardly to valve chamber 62 but is prevented from exiting out port 63 by means of ball 61 closing valve chamber 62. Instead, the fluid passes through branch 66 into valve chamber 65 past open ball 64 into valve chamber 56 past open ball 55 and out exit port 34. While FIGS. 5 through 8 illustrate two embodiments of the gravitationally actuated valved adaptor 26 in accordance with the present invention, other similarly functioning devices may be constructed which fulfill the objectives of the present invention to serially connect a drug containing vial to the delivery tube of a primary intravenous administration set.

Figure 9:
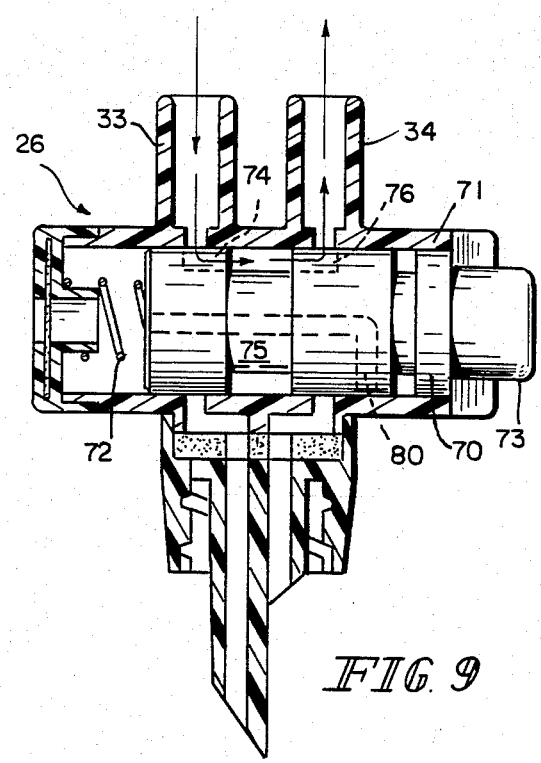
FIG. 9 is a sectional view of yet another embodiment of a valve adaptor shown in the upright bypass position.
Figure 10:
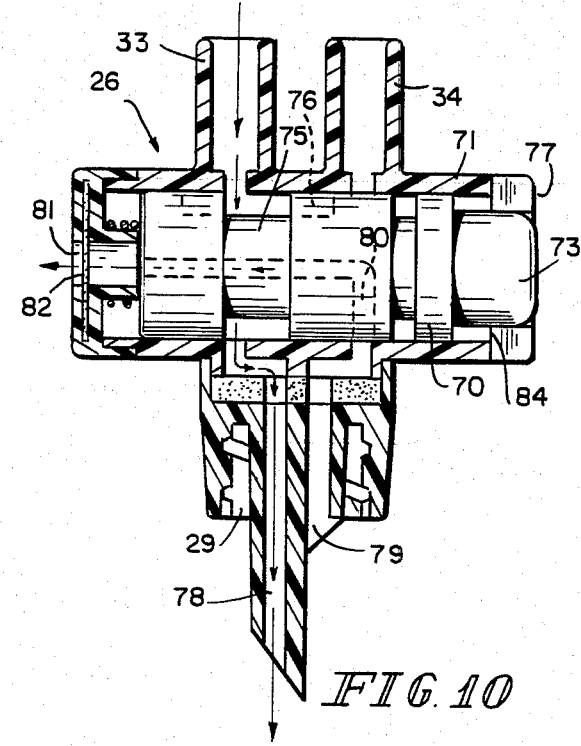
FIG. 10 is a sectional view of the valved adaptor in FIG. 9 shown in the upright vent and fill position.
Figure 11:
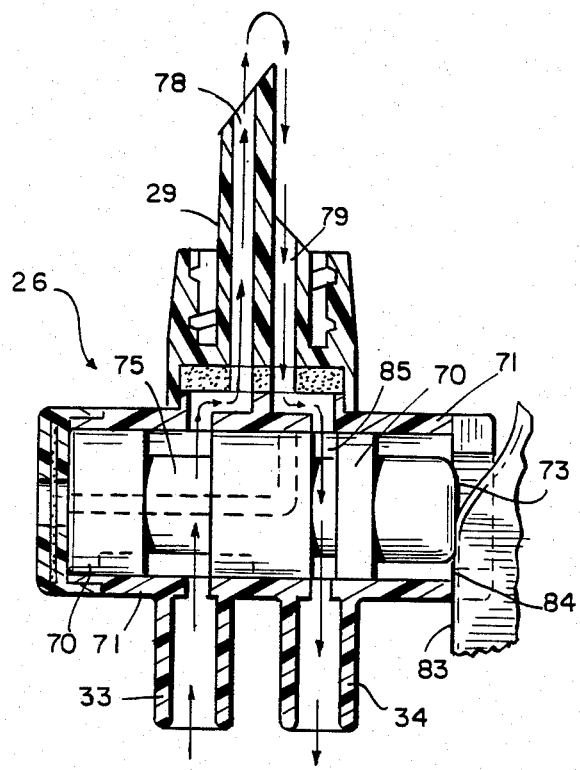
FIG. 11 is a sectional view of the valved adaptor shown in FIG. 9 in the inverted drug administering position.

FIGS. 9 through 11 illustrate yet another embodiment of the present invention in which the valved adaptor 26 includes a reciprocating spool valve 70 within a valve body 71. The body 71 includes entry port 33 and an exit port 34 which are connected to the short lengths of tubing 27 and 28 respectively. The spool valve 70 is biased toward the position shown in FIG. 9 by a spring biasing means 72 and is actuable against the spring bias by a pressure exerted on end push button 73. In the fully biased position shown in FIG. 9, fluid entering the entry port 33 is caused to flow through channel 74, central spool opening 75, and channel 76 to exit port 34. The central spool opening 75 does not communicate with any other portion of the valve and thus the fluid entering entry port 34 bypasses the remaining structure of the valved adaptor 26 and exits out exit port 34.

The push button 73 on the spool valve is manually actuable to a first position shown in FIG. 10 such that the extremity of the push button 73 is flush with the right surface 77 of valve body 71. In this position, fluid entering the entry port 33 descends directly into the central spool opening 75 while channel 76 is blocked thus preventing the fluid from exiting out exit port 34. Instead, the fluid is directed down the entry port 78 of spike 29 into a drug containing vial 32 attached in a manner as shown in FIG. 3. As the fluid enters the vial 32 through entry port 78 in spike 29, air is permitted to escape from the drug containing vial through exit port 79 and aperture 80 in the spool valve which aperture leads thru the end of the valve opposite the push button 73 to an opening 81 having an air pervious liquid barrier 82 situated therein. In this manner, the drug in the drug containing vial can be diluted from fluid in the primary I.V. container 12 to the required amount. The drug containing vial is then agitated until the drug therein is resuspended or dissolved in the liquid and ready for administration to the patient.

When the drug is ready for administration to the patient, the drug containing vial 32 and valved adaptor 26 are inverted in a holder having an automatic actuation means 83 shown in FIG. 11 which depresses the spool valve 70 against the biasing means 72 to a position even further than that shown in FIG. 10 such that the push button 73 is now flush with the bottom of slot 84 cut in the end of valve body 71. In this position, fluid entering entry port 33 enters the central spool opening 75 and through the entry port 78 in spike 29 to the interior of the drug containing vial 32. Fluid from within the vial 32 exits through opening 79 in spike 29 and is directed by a secondary spool slot 85 to exit port 34 and thence to the short tubing segment 28. The position of the spool valve 70 within valve body 71 is determined by either the manual actuation as shown in FIG. 10 or the mechanical actuation as shown in FIG. 11 against the biasing force provided by spring biasing means 72. Thus, after the interior of the vial has been washed for a period of time from fluid from the primary I.V. container 12 and all the drug originally contained therein has been administered to the patient, the valve may be returned from the position shown in FIG. 11 to that shown in FIG. 9 and the vial 32 removed from spike 29.

Figure 12:
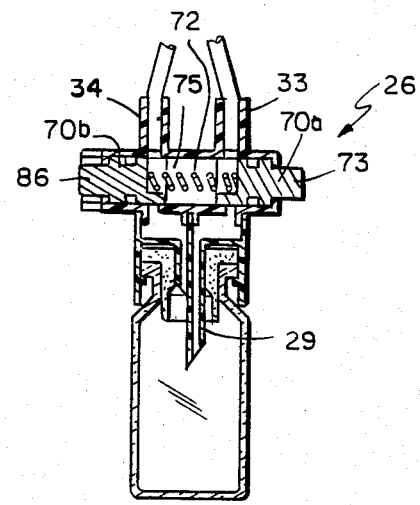
FIG. 12 is a sectional view of yet another embodiment of a valved adaptor according to the present invention.

FIG. 12 shows an alternative embodiment for a valve adaptor 26 in accordance with the present invention which functions in a manner somewhat similar to that illustrated in FIGS. 9 through 11. In FIG. 12, the spool valve is divided into a right spool 70a and a left spool 70b which are separated by a spring biasing means 72 wholly contained within the central spool opening 75. The valve adaptor 26 is shown in FIG. 12 in bypass situation analogous to that shown in FIG. 9. The depression of spool element 70a by a pressure on end 73 causes the contents of the vial 32 to be diluted in a manner similar to that shown in FIG. 10. The delivery of the contents of the drug containing vial to the patient is effected by the inversion of the vial 32 and valved adaptor 26 along with the simultaneous depression of button 73 on spool element 70a and button 86 on spool element 70b so as to cause the appropriate flow from the entry port 33 down through spike 29 and back out exit port 34. Still other variations of the basic invention employing a reciprocating spool valve may be possible for achieving the intended function of serially connecting a drug containing vial in the delivery tube of a primary intravenous administration set.

FIGS. 13–16 show yet another embodiment for a valved adaptor 26 in accordance with the present invention. The valved adaptor 26 is connected to the lower end 18 of drip chamber 14 by a short segment of flexible tubing 27 connected to entry port 33 of the valved adaptor 26. The adaptor 26 includes a body 90 having a radial platelike extension 91 having an upstanding locking collar extending around approximately 270 degrees of the plate. A drug containing vial 32 can be impaled on the spike 29 when the spike is in the far left position shown in phantom in FIG. 13. Thereafter, the spike and container can be rotated about an axis perpendicular to the plane of FIG. 13 and the locking collar 92 will act to capture the sealing ring 93 on the vial 32 and hence the vial itself.

Figure 13:
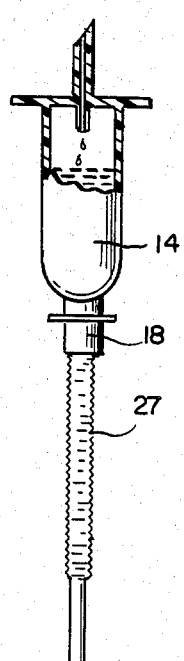
FIG. 13 is a side elevation view of yet another embodiment of a valved adaptor according to the present invention.
Figure 13:
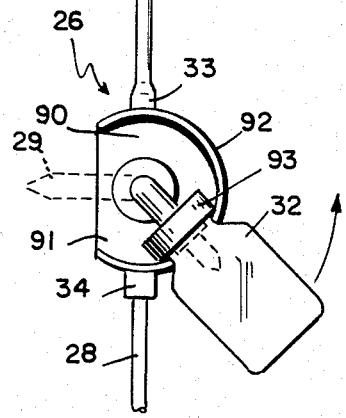
Figure 14:
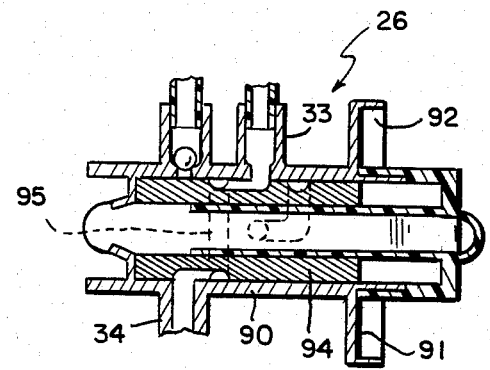
FIG. 14 is a sectional view of the valved adaptor shown in FIG. 13 with the valve situated in the bypass position.

When the spike 29 is in the position shown in phantom in FIG. 13, the spool valve 94 within the valve body 90 is in the position shown in FIG. 14. In this position, fluid from the primary intravenous administration set container 12 enters the entry port 33 and is directed by means of channel 95 directly to exit port 34 which is connected to the output tube 28. In this position, the intravenous fluid from container 12 completely bypasses the remainder of the valve system.

Figure 15:
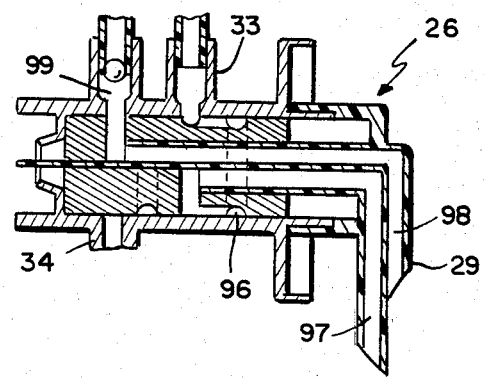
FIG. 15 is yet another sectional view of the valve adaptor shown in FIG. 13 in the fill position.

After a drug containing vial 32 is impaled on the spike 29, the contents of the vial 32 may be diluted by rotating the spike to a downwardly directed position as shown in FIG. 15. In this position, fluid entering entry port 33 is directed by channel 96 to inlet port 97 in spike 29. Simultaneously, air is permitted to exit from the vial 32 through exit port 98 in spike 29 past one-way valve 99 which opens to the atmosphere. After the desired amount of fluid enters into the drug containing vial, the vial 32 and spike 29 are rotated to a position opposite that shown in phantom in FIG. 13 and the contents agitated until the drug is suspended or dissolved in the liquid within the vial.

Figure 16:
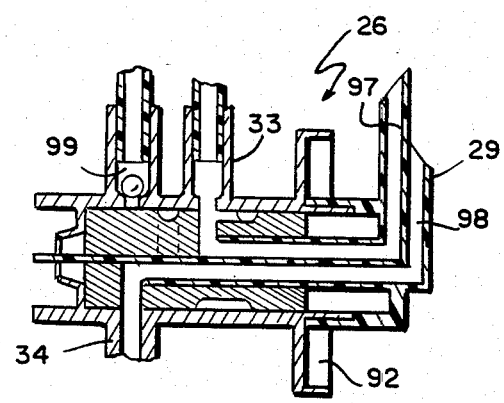
FIG. 16 is yet another sectional view of the valved adaptor shown in FIG. 13 in the inverted drug delivery position.

At such time as the drug is ready for administration to the patient, the vial and spike are rotated to an inverted position shown in FIG. 16. In this position, fluid entering the entry port is directed immediately to the inlet port 97 of spike 29 and thus into the interior of the drug containing vial 32. The contents of the vial exits directly through exit port 98 of spike 29 and out the exit port 34. The apparatus is left in this position until such time as the drugs within the vial 32 have been fully dispensed to the patient whereupon the vial 32 and spike 29 are rotated back to the phantom position illustrated in FIG. 13 and the drug vial 32 removed from the valved adaptor 26. While FIGS. 13 through 16 illustrate one possible configuration for a rotating spool valve fulfilling the objectives of the present invention, other configurations may be possible which would act to serially connect a drug containing vial in the delivery tube of a primary intravenous administration set in accordance with the objectives of this invention.

Although the invention has been described in detail with reference to certain preferred embodiments, other variations and modifications exit within the scope and spirit of the invention as described and as defined in the following claims.

What is claimed is:

1. Apparatus for connecting a vial in the delivery tube of an intravenous administration set, the set including a source of fluid connected to one end of the delivery tube, the other end of which is adapted to be inserted in a patient, the apparatus comprising:
   a valve having three operating positions and including bypass means operable in the first operating position for conducting fluid from the fluid source toward the patient, dilution means operable in the second operating position for admitting fluid from the source to the vial while permitting air to escape from the vial, and delivery means operable in the third operating position for directing the fluid from the source to pass through the vial and dilute the contents thereof while directing fluid leaving the vial to proceed through the delivery tube toward the patient.

2. The apparatus of claim 1 further comprising a reciprocating spool contained within the valve and axially slideable with respect thereto to provide said bypass, dilution, and delivery functions.

3. The apparatus of claim 1 further comprising a rotating spool within the valve pivotable with respect thereto to provide said bypass, dilution, and delivery functions.

4. The apparatus of claim 1 in which the valve provides a plurality of fixed chambers and means within the chambers responsive to gravity and movement of the valve to provide said bypass, dilution, and delivery functions.

5. The apparatus of claim 1 further comprising flexible conduit means situated between the valve and the source of fluid for permitting agitation of the vial after the admission of an initial preselected amount of fluid from the source.

6. In an intravenous administration set comprising a container containing a fluid, a delivery tube connected to the container for dispensing fluid therefrom, means for connecting the delivery tube to a patient, a drip chamber situated in the delivery tube for permitting the determination of the administration rate of the fluid, and control means for controlling the administration rate of the fluid, the improvement comprising:
   a valved adaptor for connecting a vial to the delivery tube to permit administration of the contents of the vial to the patient, the valved adaptor comprising a body, and means within the body operable between a first, second, and third position, said first position enabling the delivery of the container fluid to the patient so that the container fluid bypasses the vial, said second position enabling the dilution of the contents of the vial with said fluid, and said third position enabling the delivery of the diluted contents of the vial.

7. The valve adaptor of claim 6 wherein the vial is closed by means of a seal and the valve adapter further comprises penetration means for penetrating the seal of a vial, the penetration means including at least a pair of openings providing an entry into and an exit from the vial.

8. The valved adaptor of claim 6 further comprising first means for manually actuating the adaptor to said second position and second means for manually actuating the adaptor to said third position.

9. The valve adaptor of claim 8 wherein said second means for manually actuating the adaptor to said third position comprises means within the actuator responsive to gravity for automatically effecting the change to said third position in response to a change in the attitude of the valve body.

10. A system for the sterile administration of medicine comprising:
   a source of liquid, means to inject the liquid into a patient, means forming a passageway between the source of liquid and the injection means, control means for controlling the administration rate of the liquid to the patient, indicating means for indicating the delivery rate of liquid to the patient, and valve means for introducing the contents of a vial serially in the passageway between the source of liquid and the injection means, the valve means having three operating positions and including bypass means operable in the first operating position for conducting liquid from the liquid source toward the patient, dilution means operable in the second operating position for diluting the contents of the vial with liquid from said source, and delivery means operable in the third operating position for deliverying the diluted contents of the vial to the passageway.

11. For use with an I.V. administration set comprising a liquid source, means for injecting the liquid into a patient, and means forming a passageway from the source to the injection means, a valved adaptor for connecting a vial to the passageway, said valved adaptor having three operating positions including a first position providing bypass means for conducting liquid from the liquid source toward the patient, a manually actuable second position providing dilution means for admitting liquid from the source to the vial to dilute the contents thereof and for permitting air to escape from the vial while the admitting occurs, and an automatically actuable third position providing delivery means for directing the liquid from the source through the vial and on to the patient in response to a change in the attitude of the valved adaptor accomplished by manual movement of the valved adaptor.

* * * * *